US00PP17071P2

(12) United States Plant Patent
Trees

(10) Patent No.: US PP17,071 P2
(45) Date of Patent: Aug. 29, 2006

(54) ***ANGELONIA* PLANT NAMED 'BALANGDARPI'**

(50) Latin Name: *Angelonia angustifolia*
Varietal Denomination: Balangdarpi

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/223,630

(22) Filed: Sep. 9, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

European Plant Breeders' Rights application No. 2005/2330 filed Nov. 16, 2005.

*Primary Examiner*—Kent Bell
*Assistant Examiner*—Annette H Para
(74) *Attorney, Agent, or Firm*—Audrey Charles

(57) ABSTRACT

A new and distinct cultivar of *Angelonia* plant named 'Balangdarpi' characterized by its dark pink-colored flowers, good basal branching character, and moderately vigorous growth habit.

2 Drawing Sheets

Latin name of genus and species of plant claimed: *Angelonia angustifolia.*
Variety denomination: 'Balangdarpi'.

BACKGROUND OF THE INVENTION

The present invention relates to a new and distinct cultivar of *Angelonia* plant botanically known as *Angelonia angustifolia* and hereinafter referred to by the cultivar name 'Balangdarpi'.

The new cultivar was developed by the inventor in a controlled breeding program during May 2003 at Arroyo Grande, Calif. The objective of the breeding program was the development of *Angelonia* cultivars with freely branching, upright, and moderately vigorous growth habits, unique flower colors, and continuous flowering.

The female (seed) parent of the new cultivar was the proprietary *Angelonia angustifolia* breeding selection designated 608-B, not patented, characterized by its dark pink-colored flowers, dark green-colored foliage, and tall upright growth habit. The male (pollen) parent of the new cultivar was the proprietary *Angelonia angustifolia* breeding selection designated 608-A, not patented, characterized by its medium pink-colored flowers, dark green-colored foliage, and tall upright growth habit. The new cultivar was discovered and selected by the inventor as a single flowering plant within the progeny of the above stated cross-pollination during October 2003 in a controlled environment at Arroyo Grande, Calif.

Asexual reproduction of the new cultivar by terminal stem cuttings since October 2003 at West Chicago, Ill. has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balangdarpi' as a new and distinct cultivar of *Angelonia* plant:

1. Dark pink-colored flowers;
2. Good basal branching character; and
3. Upright growth habit.

Plants of the new cultivar differ from plants of the female parent primarily in growth habit and from plants of the male parent primarily in growth habit and flower color.

Of the *Angelonia* cultivars known to the inventor, the most similar to 'Balangdarpi' is the *Angelonia* cultivar 'Balangroki', not patented. However, in side-by-side comparisons, plants of the new cultivar differ from plants of 'Balangroki' in the following characteristics:

1. Plants of the new cultivar have lighter colored flowers compared to plants of 'Balangroki'; and
2. Plants of the new cultivar have larger flowers, as measured by length and width, compared to plants of 'Balangroki'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describe the colors of 'Balangdarpi'. The plants were grown in 10 cm pots for 11 weeks in a greenhouse at West Chicago, Ill.

DETAILED BOTANICAL DESCRIPTION

Figure 1:
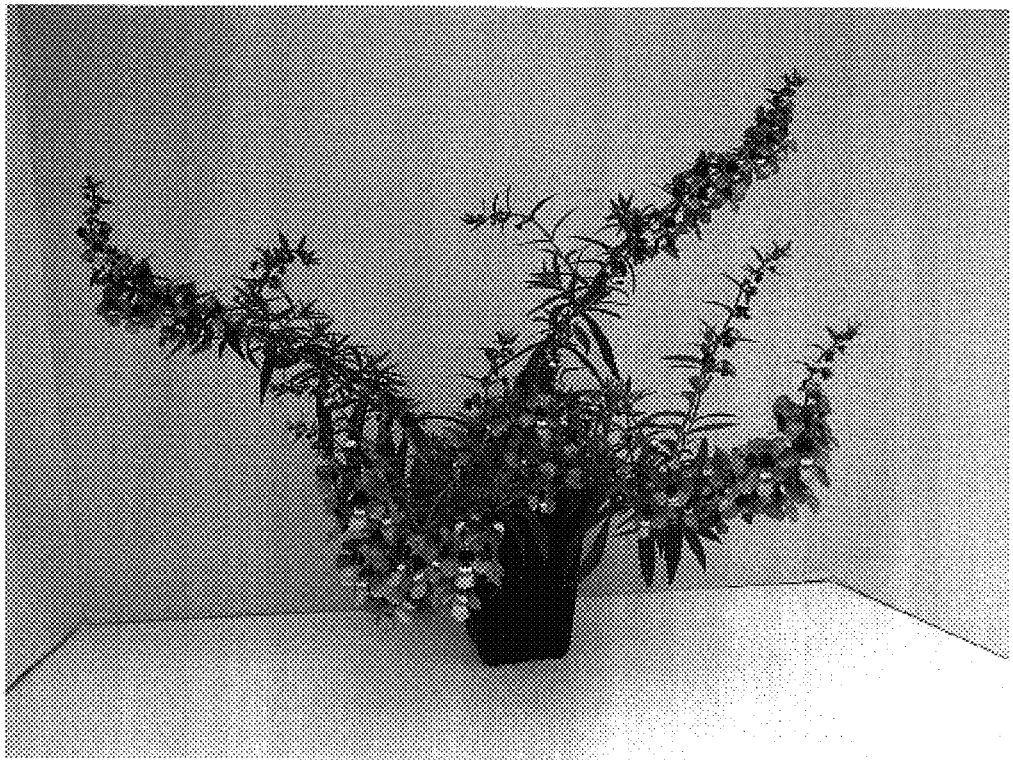
FIG. 1 illustrates a side view of the overall growth and flowering habit of 'Balangdarpi'.
Figure 2:
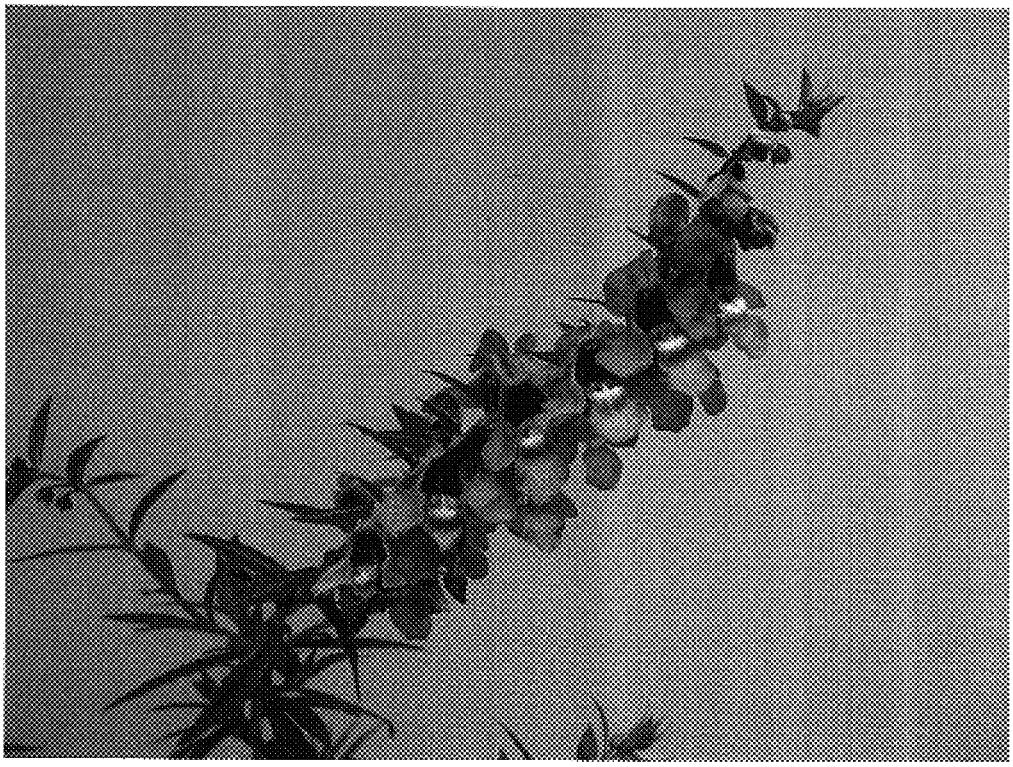
FIG. 2 illustrates a close-up view of the inflorescence of 'Balangdarpi'.
Figure 3:
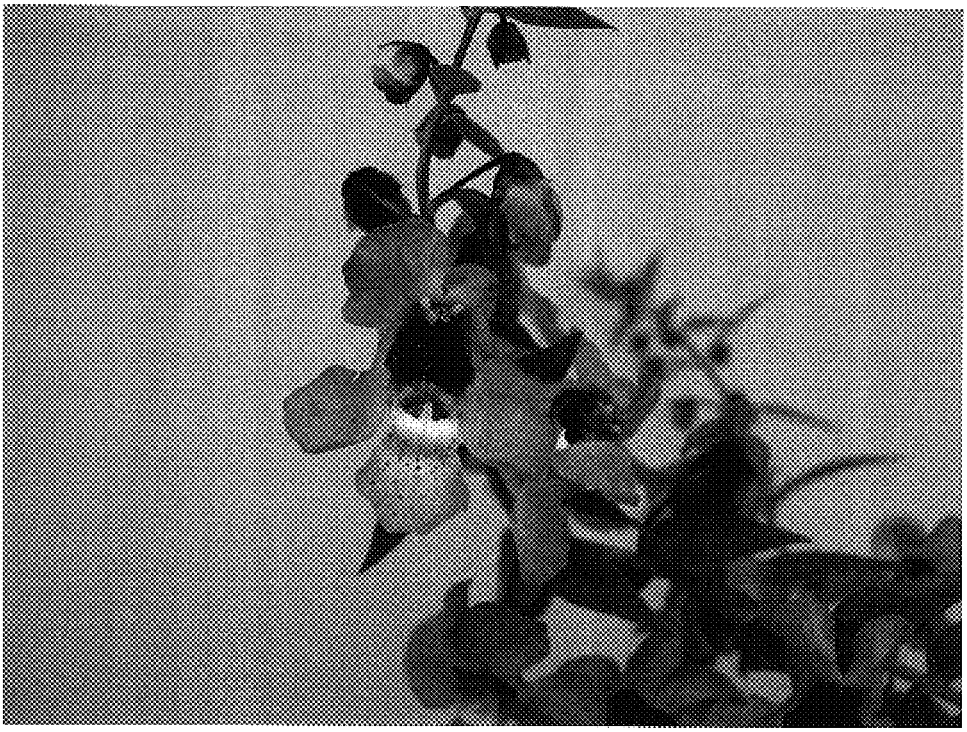
FIG. 3 illustrates a closer view of individual flowers of the inflorescence of 'Balangdarpi'.
Figure 4:
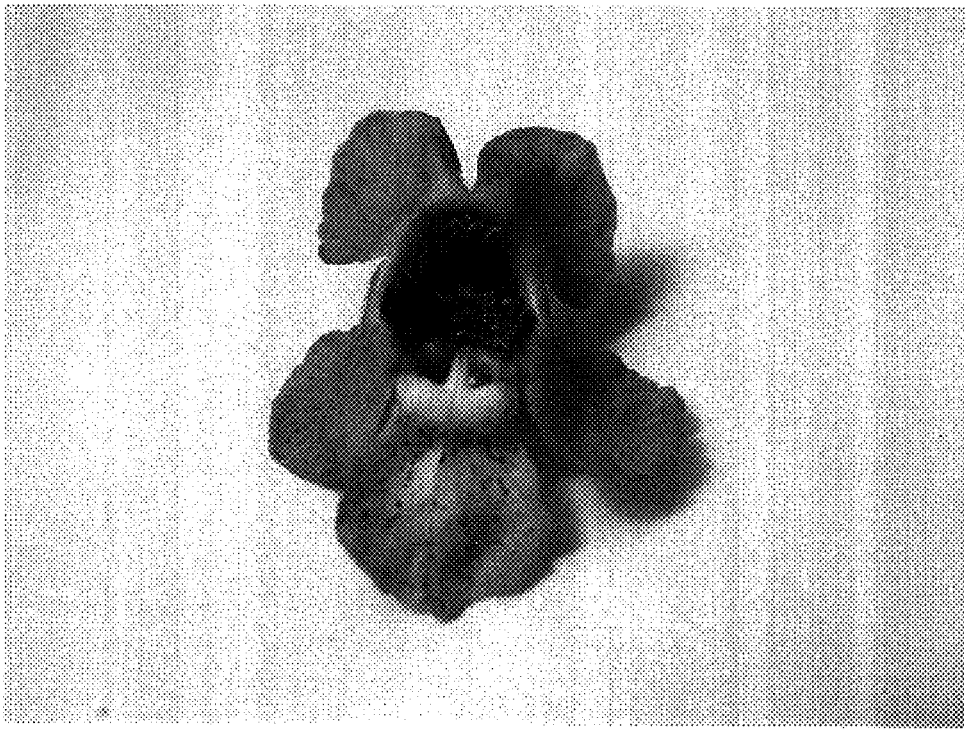
FIG. 4 illustrates a close-up view of an individual flower of 'Balangdarpi'.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Apr. 13, 2005. The readings were taken between 1:00 p.m. and 3:00 p.m. under natural light conditions.

The following descriptions and measurements describe plants produced from cuttings taken from stock plants and grown in a double polycarbonate-covered greenhouse under conditions comparable to those used in commercial practice. The plants were grown in 10 cm pots for 11 weeks while utilizing a soilless growth medium. Greenhouse temperatures were maintained at approximately 75°–85° F. (24°–29° C.) during the day and approximately 62°–70° F. (17°–21° C.) during the night. Greenhouse light levels were maintained at approximately 6,000 to 10,000 footcandles during the day.

Botanical classification: *Angelonia angustifolia*, cultivar Balangdarpi.

Parentage:

*Male (pollen) parent.*—Proprietary *Angelonia angustifolia* breeding selection 608-A, not patented.

*Female (seed) parent.*—Proprietary *Angelonia angustifolia* breeding selection designated 608-B, not patented.

Propagation:

*Type cutting.*—Terminal stem.

*Time to initiate roots.*—Approximately 7 to 9 days.

*Time to develop roots.*—Approximately 21 to 28 days.

*Root description.*—Fine and fibrous.

*Rooting habit.*—Freely branching.

Plant description:

*Crop time.*—Approximately 6 to 7 weeks from a rooted cutting.

*Habit of growth.*—Moderately vigorous with good branching.

*Form.*—Upright.

*Size.*—Height (from soil level to top of plant plane): Approximately 26.4 cm. Diameter (area of spread): Approximately 36.4 cm in diameter.

*Main branch.*—Quantity per plant: Approximately 5. Shape: Square in cross section. Strength: Strong. Length from soil level to base of raceme: Approximately 32.4 cm. Diameter: Approximately 3.1 mm. Texture: Glabrous. Color: 145B. Internode length at middle of branch: Approximately 2.1 cm.

*Foliage.*—Quantity of leaves per main branch: Approximately 22. Type: Simple. Fragrance: None. Arrangement: Opposite. Orientation to stem: Obtuse. Shape: Elliptic. Margin: Serrate. Apex: Acuminate. Base: Sessile. Length of leaf taken from middle of branch: Approximately 7 cm. Width of leaf taken from middle of branch: Approximately 1.3 cm. Texure of upper and lower surfaces: Glabrous. Venation pattern: Pinnate. Color of upper surface of young and mature foliage: Darker than 137A with venation of 143B. Color of lower surface of young and mature foliage: 137C with venation of 145C.

Flowering description:

*Flowering habit.*—'Balangdarpi' is freely flowering under outdoor growing conditions with substantially continuous blooming from spring through autumn and year round in greenhouse environment.

*Time to first flower.*—Approximately 11 weeks from planting of rooted cutting.

*Lastingness of individual bloom.*—Approximately 7 to 10 days.

*Inflorescence type/description.*—Terminal racemes. Length: 13.9 cm. Width: 4.8 cm. Number per plant: Approximately 4 open racemes per plant. Number of fully open flowers per raceme at any one time: Approximately 13.

Flower description:

*Type/fragrance.*—Bi-labiate. No fragrance.

*Bud.*—Rate of opening: 3 to 4 days from first color to fully open. Shape: Globular. Length: Approximately 9.6 mm. Diameter: Approximately 7.3 mm. Color of upper surface: 48C with 51A at base. Color of lower surface: 48C with spots of N77A.

*Flower size/aspect.*—Length: Approximately 2.5 cm. Width: Approximately 2.1 cm. Depth: Approximately 6.2 mm. Aspect: Facing outward.

*Petals.*—Quantity: Five per flower, fused at base forming a throat, an upper lip having two petals and a lower lip having three petals, one central and one lateral on each side.

*Upper lip.*—Petal apex: Obtuse. Petal margin: Entire, undulate. Length of petals: Approximately 7.2 mm. Width of petals: Approximately 9.8 mm. Color of upper and lower surfaces: First open closest to 65A, fully mature 63C. Petal texture upper surface: Densely glandular-pubescent. Petal texture lower surface: Glabrous.

*Lower lip, lateral petals.*—Petal apex: Obtuse. Petal margin: Entire. Length of petals from throat: Approximately 8.2 mm. Width of petals: Approximately 9.4 mm. Color of upper surface: First open N155B with 65A at margin, fully mature 63C. Color of lower surface: First open N155A with 65A at margin, fully mature 63C. Petal texture upper and lower surfaces: Densely pubescent with very short glandular hairs.

*Lower lip, central petal.*—Petal apex: Obtuse. Petal margin: Entire, undulate. Length of petal from palate: Approximately 8 mm. Width of petal: Approximately 9.6 mm. Color of upper and lower surfaces: First open N155B with 65A at edges, fully mature 65A at margin only, 65D in center and at base. Petal texture upper and lower surfaces: Densely pubescent with very short glandular hairs. Gland color: 13B, translucent.

*Throat.*—Length: Approximately 5.7 mm. Width: Approximately 6.8 mm. Texture of inner and outer surfaces: Glabrous. Color of inner and outer surfaces: N81D with streaks of N81A. Palate color: N155D with spots at base of N81A. Palate texture: Glabrous, pubescent along margin. Teeth color: N155D with 145B at base.

*Pedicel.*—Strength: Good. Length: Approximately 7.7 mm. Diameter: Approximately 0.7 mm. Angle to stem: Acute. Texture: Glabrous. Color: 144B with overlay of 187A.

*Calyx.*—Shape: Five-pointed star, cupped. Width: Approximately 5.0 mm. Sepal number: 5. Sepal shape: Lanceolate. Sepal margin: Entire. Sepal apex: Acuminate. Sepal length: Approximately 4.3 mm. Sepal width: Approximately 1.8 mm. Sepal texture of upper and lower surfaces: Glabrous. Sepal color of upper and lower surfaces: 143A.

*Reproductive organs.*—Androecium: Stamen quantity: Four per flower. Stamen length: Approximately 3.0 mm. Filament color: N155D. Anther shape: Bi-lobed. Anther length: Approximately 1.0 mm. Anther color: Closest to 24D. Amount of pollen: None observed. Gynoecium: Pistil quantity: One per flower. Pistil length: Approximately 3.0 mm. Stigma length: Approximately 0.5 mm. Stigma color: 150D. Style length: Approximately 1.5 mm. Style color: 155B. Ovary diameter: Approximately 1.0 mm. Ovary texture: Puberulent. Ovary color: 144C.

Seed and fruit production: Neither seed nor fruit production has been observed.

Disease and pest resistance: Resistance to pathogens and pests common to *Angelonia* has not been observed.

What is claimed is:

1. A new and distinct cultivar of *Angelonia* plant named 'Balangdarpi' substantially, as herein shown and described.

* * * * *